Figure 1:
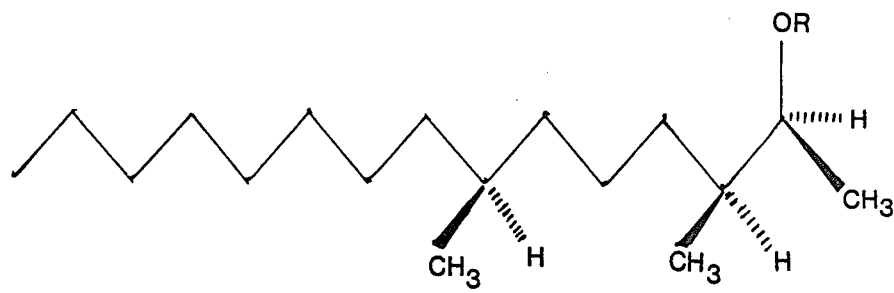

United States Patent [19]

Magnusson et al.

[11] Patent Number: 4,774,084
[45] Date of Patent: Sep. 27, 1988

[54] PHEROMONE ACTIVE COMPOUNDS

[76] Inventors: Hans G. Magnusson, Dalins väg 1, S-223 60 Lund; Jan W. Löfqvist, Murarvägen 18, S-222 30 Lund, both of Sweden

[21] Appl. No.: 834,520

[22] Filed: Feb. 28, 1986

Related U.S. Application Data

[63] Continuation of Ser. No. 614,229, May 25, 1984, abandoned.

[30] Foreign Application Priority Data

May 30, 1983 [SE] Sweden ............................ 8303047

[51] Int. Cl.$^4$ ...................... A01N 25/00; A01N 37/02
[52] U.S. Cl. ........................................ 424/84; 514/546
[58] Field of Search ........................... 424/84; 514/546

[56] References Cited

U.S. PATENT DOCUMENTS 4,474,755 10/1984 Neal, Jr. et al. ..................... 424/84

FOREIGN PATENT DOCUMENTS 2646946 4/1978 Fed. Rep. of Germany ........ 424/84

OTHER PUBLICATIONS

Chemical Abstracts 92:163511f.
Chemical Abstracts 90:86689z.
Chemical Abstracts 90:71686x.
Chemical Abstracts 89:129032d.
Chemical Abstracts 88:61919y.
Chemical Abstracts 89:107962e.
Chemical Abstracts 84:162001n.
Chemical Abstracts 99:173340h.
Chemical Abstracts 98:125687j.
Chemical Abstracts 96:6129c.
Chemical Abstracts 92:141719c.
Chemical Abstracts 88:120548y.

Primary Examiner—Albert T. Meyers
Assistant Examiner—John M. Kilcoyne
Attorney, Agent, or Firm—Burns, Doane, Swecker & Mathis

[57] ABSTRACT

The use of compounds of formula I (in 2,3-threoconfiguration)

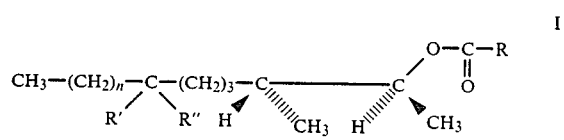

wherein n is an integer from 5 to 9, R' and R" are equal or different, and are each selected from the group consisting of hydrogen, lower alkyl, or are together O (oxygen) or =CH$_2$ (methylene), and R is lower alkyl, for the inhibition of pheromone mediated attraction between male and female of pest insects, particularly of the family Diprionidae; the use of compounds of the formula II (in 2,3-erythroconfiguration):

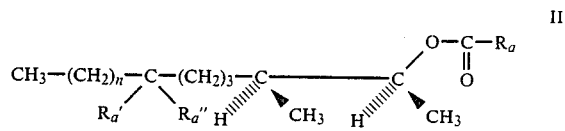

wherein n is an integer from 5 to 9, $R_a'$ is hydrogen, and $R_a''$ is lower alkyl, or $R_a'$ and $R_a''$ together form methylene, and $R_a$ is lower alkyl, as an attractant for pest insects, preferably of the family Diprionidae.

12 Claims, 5 Drawing Sheets

1: R=H
2: R=CH₃CO-
3: R=C₂H₅CO-

1: 3,7 -dimethylpentadecan-2-ol

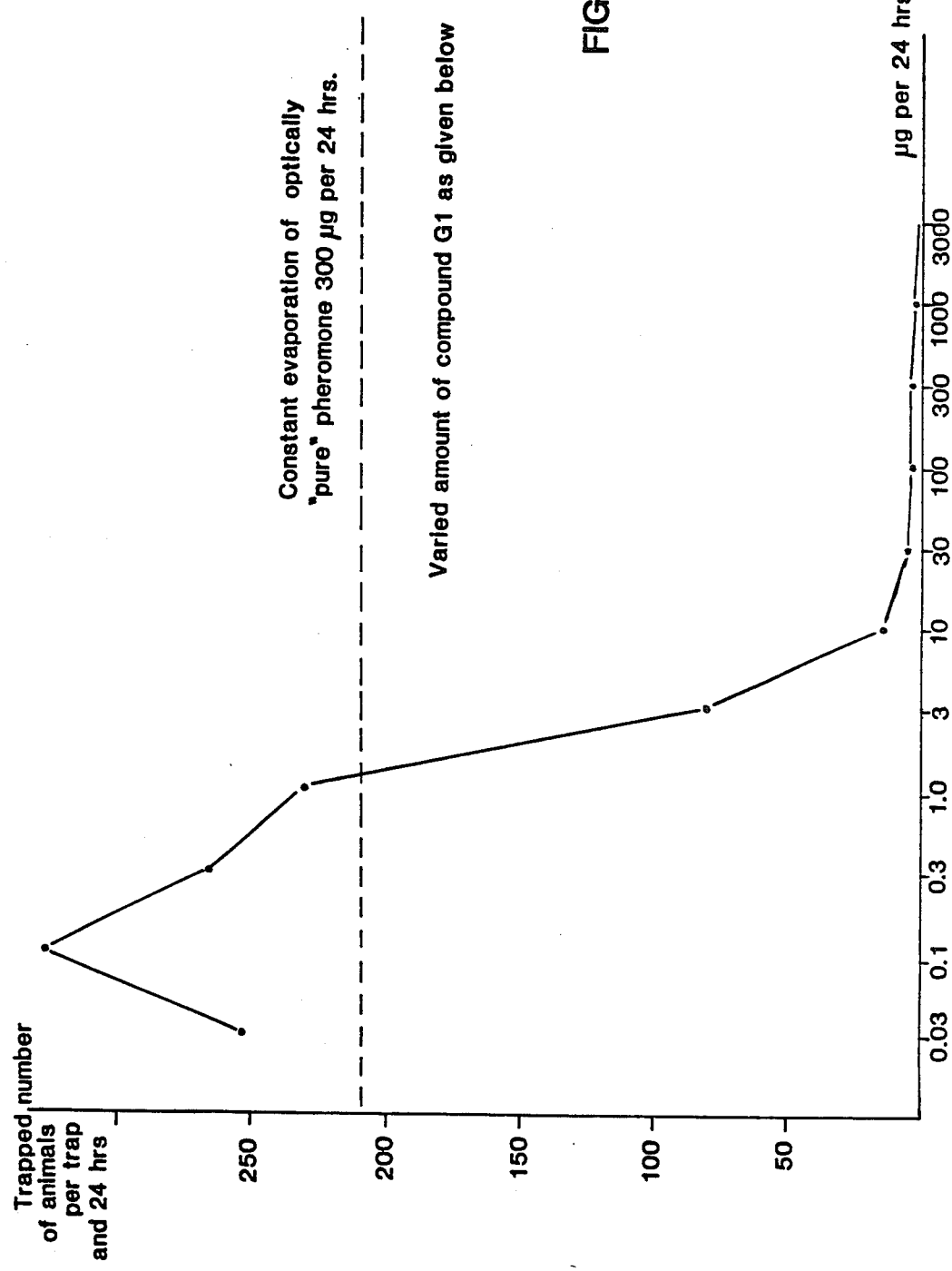

PHEROMONE ACTIVE COMPOUNDS

This application is a continuation of application Ser. No. 614,229, filed May, 25, 1984, now abandoned.

TECHNICAL FIELD

The present invention relates to the use of certain compounds as inhibitors, and attractants, respectively, for pest insects, particularly of the family Diprionidae.

The object of the present invention is to provide an effective way of determining the population of pest insects, and/or control the population of pest insects by using certain pheromone active compounds.

BACKGROUND OF THE INVENTION

The pine saw-fly, *Neodiprion sertifer*, is present in the Soviet Union, Scandinavia, and Middle Europe, as well as in Canada and the United States of America. The adult insects swarm and copulate in August to September (Scandinavia), and the females lay their eggs in the pine-needles. After wintering the eggs hatch in May. The larvae live in colonies, and eat the pine-needles. This specie shows massive population growth in cyclic intervals, which last 3 to 4 years. During such a period the larvae consume large parts of the needle-mass in a stand. All needles but the ones present on new year shots are consumed. For this reason the pines will seldom die, even if they should become next to needle-less. The attack, however, results in a considerable growth decrease, which lasts for many years.

Biological tests have shown that several species of saw-fly being closely related to the pine saw-fly, *Neodiprion sertifer*, communicates by means of pheromones, i.e. specie specific volatile communication substances. Researchers (D. M. Jewett, F. Matsumura, and H. C. Coppel, Science, 192, 51 (1976)) have shown that both acetate and propionate of 3,7-dimethylpentadecan-2-ol (Formula: cf. FIG. 1) are active as attractants in trap experiments for males of the pine saw-fly (N.s.).

Chemical synthesis of different mixtures of diastereoisomers of 3,7-dimethylpentadecan-2-ol have been reported by several research groups (G. Magnusson, Tetrahedron Letter, 31, 2713 (1977); D. M. Jewett, F. Matsumura, and H. C. Coppel, J Chem. Ecol., 4, 277 (1978); P. J. Kociensky and J. M. Ansell, J Org. Chem., 42, 1102 (1977); P. Place, M-L. Roumestant, and J. Gore, J Org. Chem., 43, 1001 (1978)).

Other researchers (K. Mori and S. Tamada, Tetrahedron Letter, 35, 1279 (1979); S. Byström, H-E. Högberg, and T. Norin, Tetrahedron, 37, 2249 (1981)) have synthetized acetates and propionates of (2S,3S,7S)-3,7-dimethylpentadecan-2-ol having 2,3-erythroconfiguration. These compounds were optically active, but not completely pure.

Furthermore, racemates of both acetates and propionates of 3,7-dimethylpentadecan-2-ol have been synthetized in erythro, as well as in threo form. (G. Magnusson, Tetrahedron, 34, 1385 (1978)).

DISCLOSURE OF THE PRESENT INVENTION

It has surprisingly been shown that certain closely related structures have an ability of inhibiting the pheromone mediated attraction between males and females of pest insects. Within the present investigations it has now been shown that compounds of the general formula I has this inhibiting activity, viz:

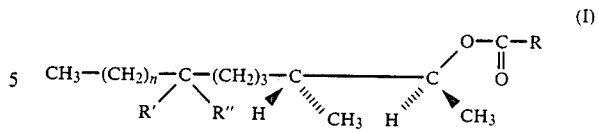

wherein n is an integer from 5 to 9, R' and R" are equal or different, and are selected from the group consisting of hydrogen, lower alkyl having 1 to 3 carbon atoms, or form together O (oxygen), or =CH₂ (methylene), and R is selected from the group consisting of lower alkyl groups having 1 to 3 carbon atoms. All these compounds having an inhibiting effect are present in 2,3-threo configuration for pine saw-fly (N.s.).

R in the formula I is preferably methyl or ethyl. Further, R', and R" in formula I are together preferably forming a methylene group.

Preferred compounds are those wherein n, in formula I, is 7.

A particularly preferred embodiment of the compounds of formula I is the one wherein R' is hydrogen, and R", and R are both methyl, and n is 7.

Continued investigations have, moreover, shown that certain compounds being closely related to the naturally occurring pheromones show an attracting ability which exceeds that of the naturally occurring ones. According to another further object of the present invention a compound of the general formula II is thus used as an attractant for pest insects, particularly of the family Diprionidae, more particularly of the genus Neodiprion, viz:

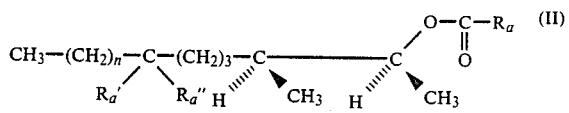

wherein n is an integer from 5 to 9, $R_a'$ is hydrogen, and $R_a''$ is lower alkyl having 1 to 3 carbon atoms, or $R_a'$ and $R_a''$ together form =CH₂ (methylene), and $R_a$ is selected from the group consisting of lower alkyl groups having 1 to 3 carbon atoms. All these compounds of the general formula II are present in 2,3-erythro configuration.

$R_a$ in formula II is preferably methyl or ethyl. Further, $R_a'$ and $R_a''$ in formula II are together preferably methylene (=CH₂), and n is preferably 7.

Excluded from the formula II-compounds above are those, wherein n is 7, and $R_a'$ is hydrogen and $R_a''$ is methyl.

The use of compounds of Formulae I, and II is particularly directed against pest insects of the family Diprionidae, and more particularly against those of the genus Neodiprion, and even more particularly against the pine saw-fly (N.s.) and relates to technique based upon pheromone mediated attraction between the sexes, and inhibition thereof. More particular, the invention provides application both for population determination by means of traps (prognosis), and for control of population by means of confusion based on pheromones or their analogues (Management of Insect Pests with Semiochemicals; Concepts; and Practise; E. R. Mitchell, Editor, Plenum Press 1981).

The invention will be described more in detail in the following, however, without being restricted thereto.

The compounds of the invention in general and those described below have all been synthetized according to the methods described by G. Magnusson, Tetrahedron Letter, 31, 2713 (1977) and G. Magnusson, Tetrahedron, 34, 1385 (1978).

EXAMPLE 1

Inhibitory effect

The use of compounds of the present invention for obtaining an inhibitory effect was tested in a field test at which glue traps were used. The male saw-flies that were caught in the traps were counted daily. As attractant was chosen an optically pure enantiomer (2S,3S,7S9-3,7-dimethylpentadecan-2-yl acetate, which was evaporated from capillaries at a rate of about 300 µg per 24 hrs. This attractant was combined in the trap with a second capillary comprising the racemate of the corresponding threo-form (compound $G_1$ according to the enclosed FIG. 2) in an amount varying from about 3000 µg per 24 hrs to about 0.03 µg per 24 hrs. As a control one trap without any compound at all was used, as well as a trap loaded with the attractant only. The results from this test is shown in FIG. 5. The experiment was run in three replicates over 96 hrs with trapped males counted daily.

These traps loaded with the attractant only caught about 200 saw-flies, males, per 24 hrs as a mean value. The threo-form ($G_1$) inhibited the attraction ability of the attractant completely so that practically no saw-flies were caught at all down to a release rate of 10 µg per 24 hrs of evaporation of the threo-form.

EXAMPLE 2

Figure 2:
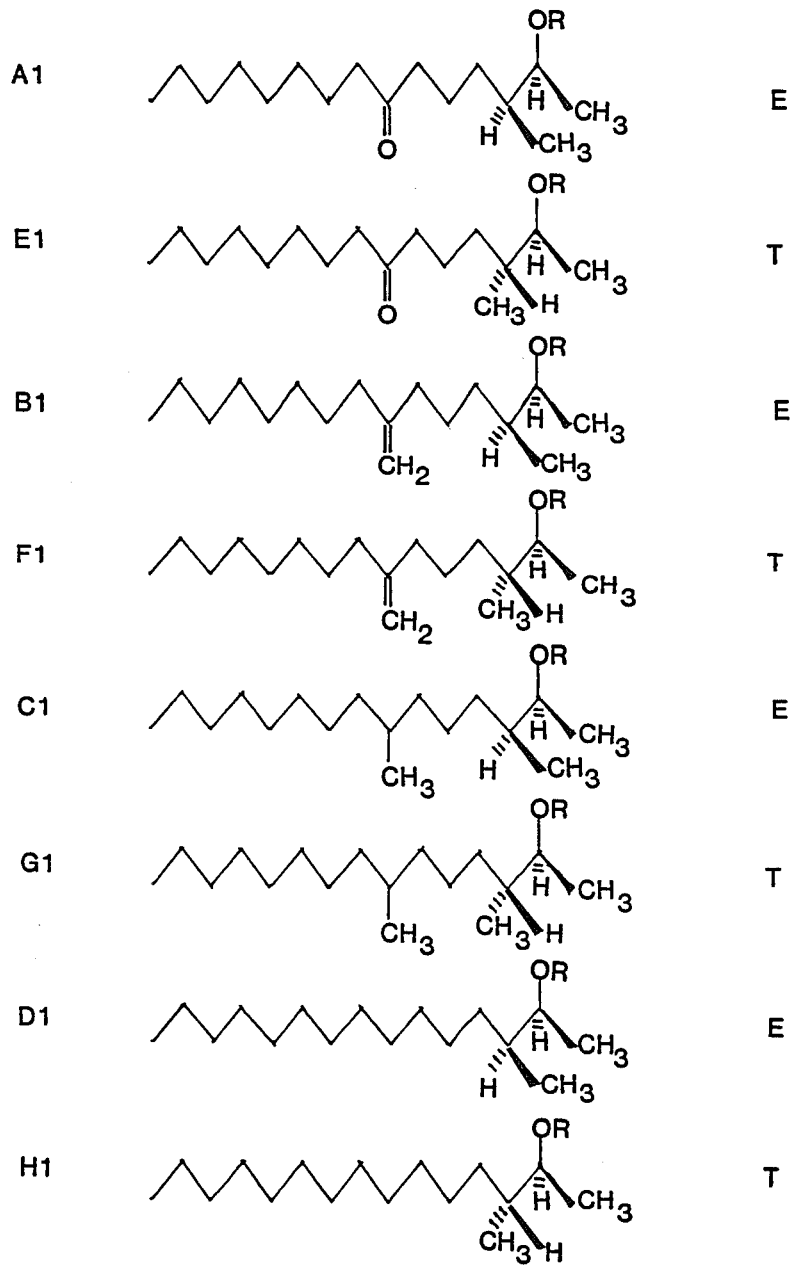

Example 1 was repeated, this time using the racemate of the threo-form $F_1$ of FIG. 2. In this case the attraction ability of the attractant was almost completely inhibited.

EXAMPLE 3

Example 1 was repeated, this time using the racemate of the threo-form $F_2$ of FIG. 2. The attraction ability of the attractant was inhibited in an effective way for practical use.

EXAMPLE 4

Attraction effect

The possibility of an attraction effect was tested in glue traps. The substances were released from capillaries at a rate of about 300 µg per 24 hrs. Each trap was loaded with one compound, and for each compound three traps were used. As a control an unloaded trap was used. The test were run for a time period of 72 hrs, whereby attracted and trapped saw-flies were counted daily.

During the first 72 hrs compounds $A_1$–$H_1$ of FIG. 2 were tested in three replicates. The results are given in FIG. 3. Compound $B_1$ was by far the most superior attractant, in spite of the fact that this compound is not the one present in Nature.

During the subsequent 72 hrs compounds $A_2$–$H_2$ were tested in three replicates. These compounds correspond to compounds $A_1$–$H_1$ with the exception that they have $R_a$ equal to ethyl instead of methyl, i.e. they are propionates instead of acetate. The test series was extended with $B_1$, which was a control checking that the swarming intensity was similar during the two testing periods. The results obtained in the tests are given in FIG. 4.

Figure 3:
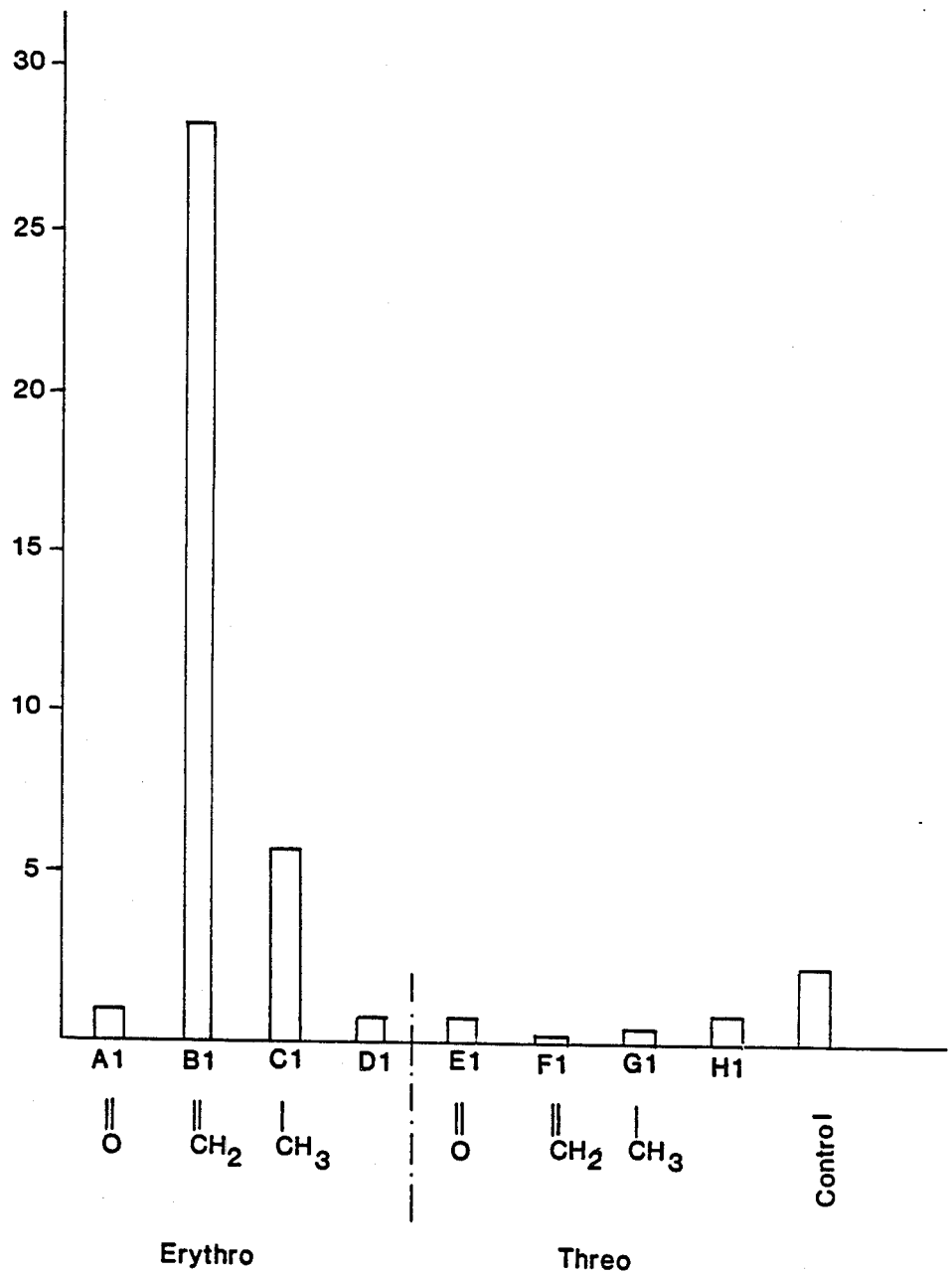
Figure 4:
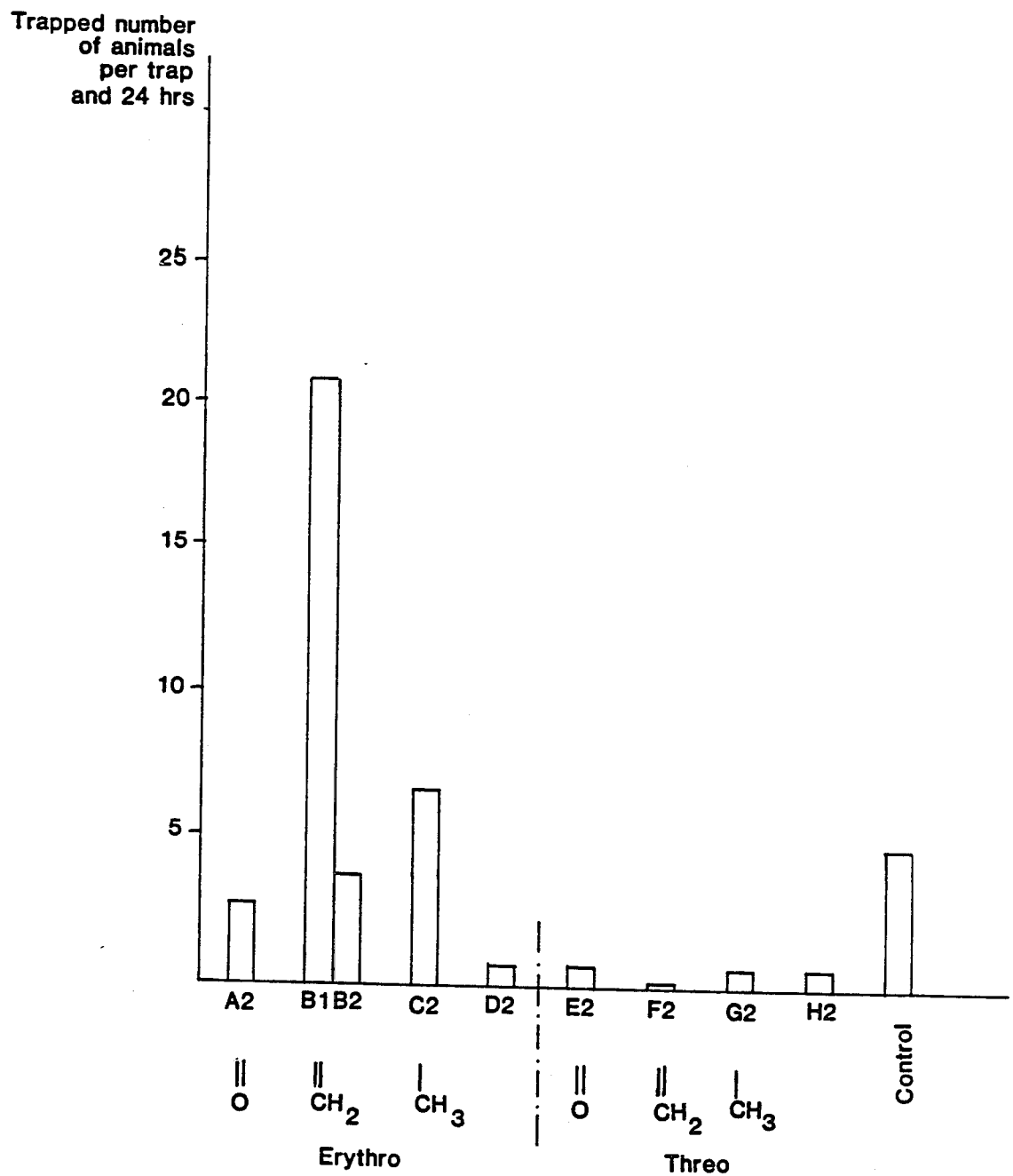

It is evident from FIG. 3 and FIG. 4 that compounds $B_1$, $C_1$, and $C_2$, only, caught more saw-flies than the unloaded control traps. It is further evident from the test results that compound $B_1$ is a much stronger attractant than $G_1$, Compounds $C_1$, and $C_2$ are active attractants even as racemates, and should be even more so when used in optically pure form.

The tests above show that the compounds given herein are very effective ones, and it has been calculated that the amounts of active compound evaporated over a hectare is one in the order of milligrammes. Using the compounds for population determinations or for confusion purposes it is evident that 1 to 10 grammes of the compounds per hectare will be sufficient to reach a more than acceptable result.

We claim:

1. A method of inhibiting attraction between male and female insects of the family Diprionidae comprising exposing said insects by evaporation from a trap to a compound of formula I in 2,3-threoconfiguration:

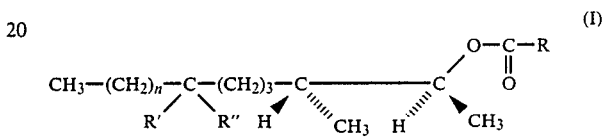

wherein n is an integer from 5 to 9, R' and R" are independently selected from the group consisting of hydrogen and lower alkyl having 1 to 3 carbon atoms, or form together O or =CH₂, and R is selected from the group consisting of lower alkyl groups having 1 to 3 carbon atoms, in an amount sufficient to inhibit the pheromone mediated attraction between said insects.

2. The method of claim 1 wherein R is methyl or ethyl.

3. The method of claim 1 wherein R' and R" together form a methylene group.

4. The method of claim 1 wherein n is 7.

5. The method of claim 1 wherein R' is hydrogen, R" and R are methyl, and n is 7.

6. The method of claim 1 wherein the pheromone mediated attraction is inhibited between male and female insects of the genus Neodiprion.

7. The method of claim 6 wherein the pheromone mediated attraction is inhibited between male and female insects of the pinesaw fly *Neodiprion sertifer*.

8. A method of attracting insects of the family Diprionidae comprising exposing said insects by evaporation from a trap to a compound of the formula II, in 2,3-erythro-configuration:

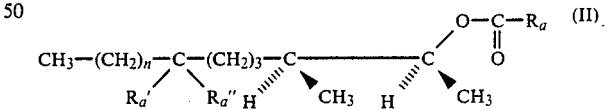

wherein n is an integer from 5 to 9, $R_a$ is methyl, $R_a'$ is hydrogen, and $R_a''$ is lower alkyl selected from the group consisting of lower alkyl groups having 1 to 3 carbon atoms or $R_a'$ and $R_a''$ together form =CH₂ with the proviso that n is not 7 when $R_a'$ is hydrogen and $R_a''$ is methyl, in an amount sufficient to attract said insects.

9. The method of claim 8 wherein $R_a'$ and $R_a''$ together form a methylene group.

10. The method of claim 8 wherein n is 7.

11. The method of claim 8 wherein the insects are of the genus Neodiprion.

12. The method of claim 11 wherein the insects are the pinesaw fly *Neodiprion sertifer*.

* * * * *